United States Patent [19]
Volkmann

[11] Patent Number: 6,022,978
[45] Date of Patent: *Feb. 8, 2000

[54] BENZIMIDAZOLE DERIVATIVES

[75] Inventor: Robert A. Volkmann, New York, N.Y.

[73] Assignee: Pfizer Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/821,750

[22] Filed: Mar. 20, 1997

Related U.S. Application Data

[60] Provisional application No. 60/019,587, Jun. 11, 1996.

[51] Int. Cl.$^7$ ............ C07D 235/28; C07D 235/24; C07D 235/14; C07D 235/10
[52] U.S. Cl. .............. 548/307.1; 548/304.4; 548/309.7; 548/310.1; 548/310.4
[58] Field of Search .................. 548/304.4, 309.7, 548/310.1, 310.4

[56] References Cited

U.S. PATENT DOCUMENTS 5,140,055  8/1992  Hirata et al. ................ 524/93

OTHER PUBLICATIONS

Stecherbina et al, "Theoretical Study of Spectral–, etc" CA 101 : 22834f, 1984.
Watts et al, "Identification of non–volatile organics, etc" CA 101 :177042, 1984.
Atkinson et al, "Synthesis of some phenyl cinnolines, etc" CA 54 : 3440c, 1960.

*Primary Examiner*—Patricia L. Morris
*Attorney, Agent, or Firm*—Peter C. Richardson; Paul H. Ginsburg; Seth H. Jacobs

[57] ABSTRACT

Benzimidazole Derivatives having the formulae

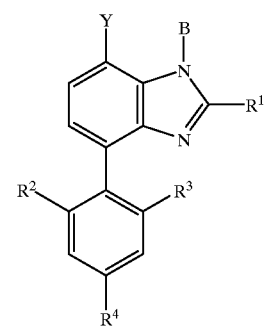

wherein B, Y, $R^1$, $R^2$, $R^3$ and $R^4$ are as defined in the specification. These compounds and their pharmaceutically acceptable salts are useful in the treatment of CNS and stress related disorders.

13 Claims, No Drawings

BENZIMIDAZOLE DERIVATIVES

This application claims priority under 35 U.S.C. §119(e) of U.S. patent application Ser. No. 60/019,587, filed Jun. 11, 1996.

BACKGROUND OF THE INVENTION

This invention relates to novel benzimidazole derivatives, pharmaceutical compositions containing them, and methods of using them to treat certain central nervous system (CNS) and other disorders. The compounds of this invention are corticotropin releasing factor (CRF) receptor antagonists.

CRF antagonists are referred to in U.S. Pat. Nos. 4,605,642 and 5,063,245, which relate, respectively, to peptides and pyrazolinones, and were issued, respectively, on Aug. 12, 1986 and Nov. 5, 1991. They are also referred to in the following: PCT patent application No. PCT/IB95/00439, which designates the United States and was filed on Jun. 6, 1995; PCT patent application No. PCT/IB95/00373, which designates the United States and was filed on May 18, 1995; U.S. patent application No. 08/448,539, which was filed in the PCT on Nov. 12, 1993 and entered the U.S. national phase on Jun. 14, 1995; U.S. patent application No. 08/481,413, which was filed in the PCT on Nov. 26, 1993 and entered the U.S. national phase on Jul. 24, 1995; and U.S. patent application No. 08/254,820, which was filed on Apr. 19, 1995. All the foregoing patents and patent applications are incorporated herein by reference in their entireties.

The importance of CRF antagonists Is discussed in the literature, e.q., as discussed in U.S. Pat. No. 5,063,245, which is incorporated herein by reference in its entirety. A recent outline of the different activities possessed by CRF antagonists is found in M. J. Owens et al., *Pharm. Rev., Vol.* 43, pages 425 to 473 (1991), also incorporated herein by reference. Based on the research described in these two and other references, CRF antagonists are effective in the treatment of a wide range of stress-related illnesses, such as depression, anxiety, headache, irritable bowel syndrome, inflammatory diseases, immune suppression, Alzheimer's disease, gastrointestinal diseases, anorexia nervosa, hemorrhagic stress, drug and alcohol withdrawal symptoms, drug addiction, infertility, head trauma, stroke, and stress-induced infections in humans and animals.

SUMMARY OF THE INVENTION

The present invention relates to a compound of the formula

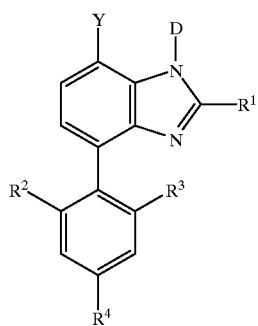

I wherein D is hydrogen or $(C_1-C_{10})$ straight or branched aklyl;

Y is hydrogen or methyl;

$R^1$ is hydrogen, halo, —S—$(C_1-C_{10})$alkyl or $(C_1-C_{10})$ straight or branched alkyl, wherein said alkyl may optionally be substituted with one or more substituents selected from halo, —S$(C_1-C_4)$alkyl, amino, —NH$(C_1-C_4)$alkyl and —N$[(C_1-C_4)$alkyl$]_2$; and $R^2$, $R^3$ and $R^4$ are selected, independently, from hydrogen, fluoro, chloro, $(C_1-C_6)$ alkyl and $(C_1-C_6)$alkoxy; or two of $R^2$, $R^3$, and $R^4$ are hydrogen and the other is selected from hydroxy, iodo, bromo, formyl, cyano, nitro, trifluoromethyl, amino, $(C_1-C_6)$alkyl-O—$(C_1-C_6)$alkyl, —NHCH$_3$, —N(CH$_3)_2$, —COOH, —COO$(C_1-C_4)$alkyl —CO$(C_1-C_4)$ alkyl, —SO$_2$—NH$(C_1-C_4)$alkyl, SO$_2$—N$[(C_1-C_4)$alkyl$]_2$, —SO$_2$NH$_2$, —NHSO$_2$—$(C_1-C_4)$alkyl, —S$(C_1-C_6)$alkyl and —SO$_2$—$(C_1-C_6)$alkyl, and wherein the $(C_1-C_4)$ and $(C_1-C_6)$alkyl moieties in the foregoing $R^2$, $R^3$ and $R^4$ groups may optionally be substituted with one or two fluoro groups or with one substituent selected from hydroxy, amino, methylamino, dimethylamino and acetyl;

and the pharmaceutically acceptable salts of such compounds.

Preferred embodiments of this invention include compounds of the formula I wherein $R^2$, $R^3$, and $R^4$ are methyl, $R^1$ is methyl, ethyl or chloro, and B is diethylmethyl.

Other more specific embodiments of this invention include the following:

(a) compounds of the formula I wherein Y is hydrogen;

(b) compounds of the formula I wherein $R^2$, $R^3$ and $R^4$ are selected from hydrogen, fluoro, chloro and $(C_1-C_3)$alkyl;

(c) compounds of the formula I wherein D is hydrogen;

(d) compounds of the formula I wherein Y is hydrogen and $R^1$ is hydrogen, halo, —S—$(C_1-C_6)$alkyl or $(C_1-C_6)$ straight or branched alkyl; and (e) compounds of the formula I wherein D is $(C_1-C_4)$ straight or branched alkyl.

The compounds of formula I have chiral centers and therefore exist in different enantiomeric forms. This invention relates to all optical isomers (e.g., enantiomers and diastereomers) and all other stereoisomers of compounds of the formula I, as well as racemic and other mixtures thereof.

Formula I above includes compounds identical to those depicted but for the fact that one or more hydrogen or carbon atoms are replaced by isotopes thereof. Such compounds are useful as research and diagnostic tools in metabolism pharmokinetic studies and in binding assays.

The present invention also relates to the pharmaceutically acceptable acid addition and base salts of compounds of the formula I. The acids that may be used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesuffonate, ethanesuffonate, benzenesulfonate, p-toluenesutfonate and pamoate [i.e., 1,1'-methylene-bis-(2-hydroxy--naphthoate)] salts.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "one or more substituents," as used herein, includes from one to the maximum number of substituents possible based on the number of available bonding sites.

The invention also relates to a pharmaceutical composition for the treatment of (a) a disorder the treatment of which can be effected or facilitated by antagonizing CRF at its receptor sites, including but not limited to disorders induced or facilitated by CRF, or (b) a disorder selected from inflammatory disorders such as rheumatoid arthritis and osteoarthritis, pain, asthma, psoriasis and allergies; osteoporosis; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, premenstrual dysphoric disorder, mood disorders associated with premenstrual syndrome, postpartum depression and dysthemia; bipolar disorders; cyclothymia; fatigue syndrome; stress-induced headache; psychosocial dwarfism; cancer; irritable bowel syndrome, Crohn's disease; ulcer; diarrhea; spastic colon; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); stress induced fever; muscular spasms; urinary incontinence; cardiovascular and heart related disorders such as hypertension, tachycardia and congestive heart failure; senile dementia of the Alzheimers type; multiinfarct dementia; amyotrophic lateral sclerosis; and hypoglycemia in a mammal, including a human, comprising an amount of a compound of the formula I, or a pharmaceutically acceptable salt thereof, that is effective in the treatment of such disorder, and a pharmaceutically acceptable carrier.

The invention also relates to a method for the treatment of (a) a disorder the treatment of which can be effected or facilitated by antagonizing CRF at its receptor sites, including but not limited to disorders induced or facilitated by CRF, or (b) a disorder selected from inflammatory disorders such as rheumatoid arthritis and osteoarthritis, pain, asthma, psoriasis and allergies; osteoporosis; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, premenstrual dysphoric disorder, mood disorders associated with premenstrual syndrome, postpartum depression and dysthemia; bipolar disorders; cyclothymia; fatigue syndrome; stress-induced headache; psychosocial dwarfism; cancer; irritable bowel syndrome; Crohn's disease; ulcer; diarrhea; spastic colon; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress In sheep or human-animal interaction related stress In dogs); stress induced fever, muscular spasms; urinary incontinence; cardiovascular and heart related disorders such as hypertension, tachycardia and congestive heart failure; senile dementia of the Alzheimers type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; and hypoglycemia in a mammal, including a human, comprising administering to a subject in need of said treatment an amount of a compound of the formula I, or a pharmaceutically acceptable salt thereof, that is effective in treating such disorder.

This invention also relates to a pharmaceutical composition for preventing premature birth in a mammal, including a human, comprising an amount of a compound of the formula I, or a pharmaceutically acceptable salt thereof, that is effective in preventing premature birth, and a pharmaceutically acceptable carrier.

This invention also relates to a method of preventing premature birth in a mammal, including a human, comprising administering to said mammal an amount of a compound of the formula I, or a pharmaceutically acceptable sat hereof, that is effective in preventing premature birth.

The term "preventing premature birth," as used herein, refers to both preventing a birth from occurring prematurely and to delaying the occurrence of a premature birth.

DETAILED DESCRIPTION OF THE INVENTION

The compounds of the formula I may be prepared as described in the following reaction schemes and discussion. Unless otherwise indicated, $R^1$, $R^2$, $R^3$, $R^4$, and D in the reaction schemes and discussion that follow are defined as above.

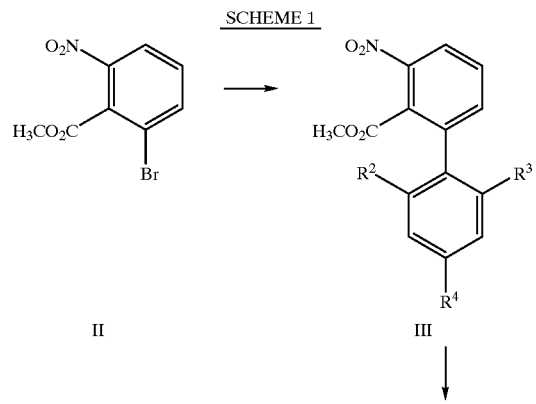

-continued
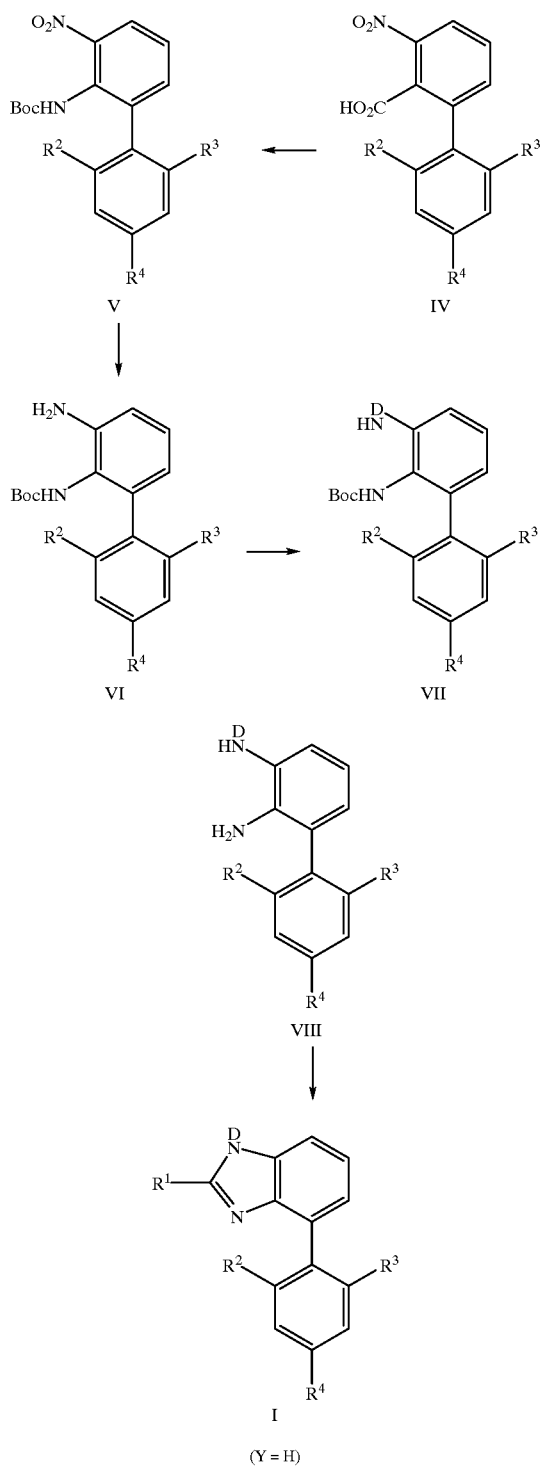
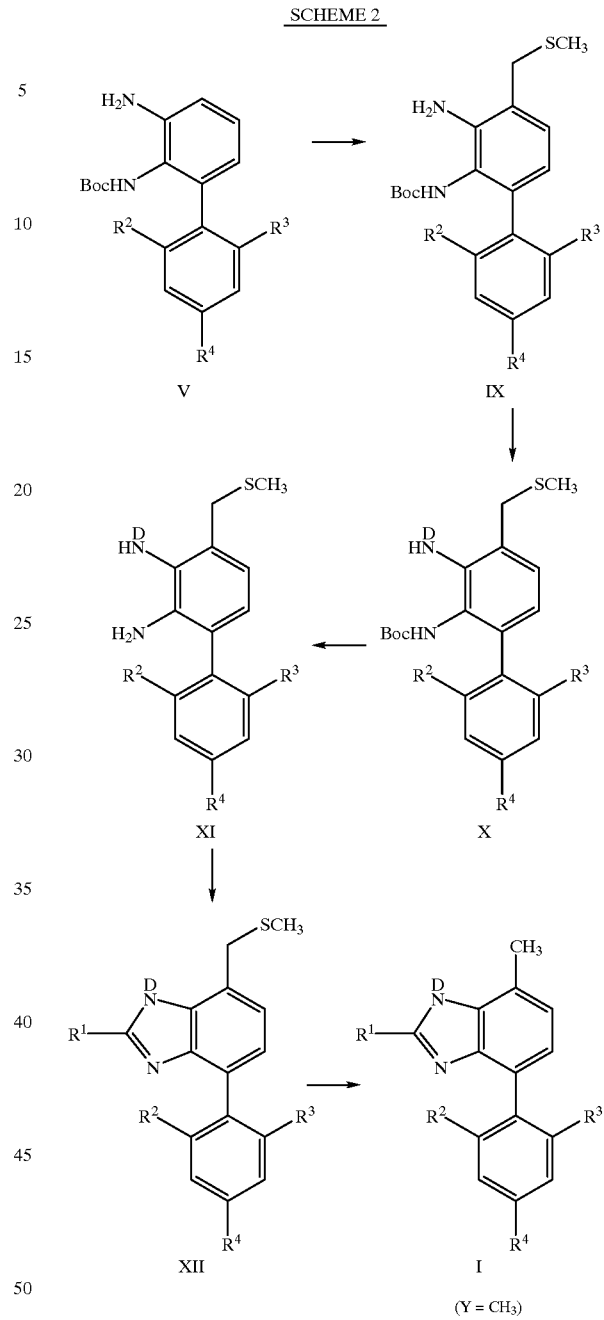
Scheme 1 illustrates a method of preparing compounds of the formula I wherein Y is hydrogen.
Referring to Scheme 1, 2-bromo-5-nitrobenzoic acid methyl ester (II) is reacted with a compound of the formula

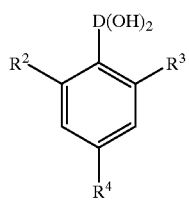

XIII in the presence of a tetrakis (triphenylphosphine)palladium (O) catalyst and cesium fluoride to form a compound of the formula III. The preferred solvent for this reaction is dimethoxyethane (DME), but other reaction inert solvents such as ethyl ether ("ether") and tetrahydrofuran (THF) may also be used. Preferably, the reaction is begun at about room temperature and then the reaction mixture is heated to reflux.

The compound of formula III is then hydrolysed, using standard methods well known in the art, to form the corresponding acid of formula IV. For example, the compound of formula III can be reacted with sodium hydroxide in a methanol/water solvent and heated to reflux.

The acid of formula IV can be converted into the protected amine of formula V by reacting it with diphenylphosphorylazide in an inert solvent such as anhydrous benzene or anhydrous toluene, in the presence of a tertiary amine base such as triethylamine, and, after allowing the reaction mixture to reflux for about one hour, cooling the mixture and adding t-butanol. This reaction generally carried out at a temperature from about 50° C. to about the reflux temperature of the reaction mixture.

Alternative nitrogen protecting groups and methods for adding and removing them can be found in T. Greene, *Protecting Groups in Organic Synthesis,* John Wiley & Sons, New York, 1991.

Reduction of the resulting compound of formula V formed in the above step, using standard methods well known in the art, yields the corresponding compound of formula VI. This reduction can be accomplished, for example, using hydrogen in the presence of a catalyst such as Raney nickel or palladium on carbon, in a reaction inert solvent such as methanol, ethanol or ethyl acetate, at an initial pressure of from about one to about four atmospheres and at a temperature of about 0° C. to about 60° C. Typically, the reaction is conducted with methanol as the solvent and with about three atmospheres of hydrogen gas pressure at room temperature for about 0.5 to 1.0 hours.

Reaction of the compound of formula VI with the appropriate aldehyde or ketone for adding substituent B to the nitrogen of the free amino group, in the presence a reducing agent and dehydrating agent, yields the corresponding compound of formula VII. The aldehyde or ketone is chosen so that the carbonyl carbon atom will be the point of attachment of group B to the free amino nitrogen. This reaction is carried out under anhydrous conditions using a dehydrating agent such as sodium sulfate or magnesium sulfate. Suitable reducing agents include sodium triacetoxyborohydride and sodium cyanoborohydride. Sodium triacetoxyborohydride is preferred. Suitable solvents include acetic acid, acetonitrile and methanol. Acetic acid is the preferred solvent. The reaction temperature can range from about 0° C. to about 60° C. and is preferably about 23° C.

The corresponding compound of formula VIII can be formed by removal of the t-butoxycarbonyl protecting group. This can be accomplished using standard methods well known in the art, for example, using trifluoroacetic acid in methylene chloride, or hydrochloric acid in water.

The desired compound of formula I can be formed by reacting the corresponding compound of formula VIII with an ortho acid derivative of the formula $(CH_3CH_2O)_3CR^1$. This reaction is generally carried out in the presence of an acid catalyst such as concentrated hydrochloric acid, hydrobromic acid or nitric acid, preferably concentrated hydrochloric acid, at a temperature from about 5° C. to about 60° C., preferably at about 23° C.

Scheme 2 illustrates a method of preparing compounds of the formula I wherein Y is methyl.

Referring to Scheme 2, a compound of the formula V is reacted with dimethyl disulfide and N-chlorosuccinamide to form the corresponding compound having formula IX. This reaction is generally carried out in an aprotic solvent such as methylene chloride, chloroform or dichloroethanes, preferably methylene chloride, at a temperature from about 0° C. to about 50° C., preferably at about 40° C.

The deprotection step, which yields the corresponding compound of formula X and the amino substitution step, which yields the corresponding compound of formula XI, may be accomplished using procedures analogous to those illustrated in Scheme 1 and described above.

Compounds of the formula I wherein Y is $CH_3$ can be formed by reducing the corresponding compounds of formula XII. This reduction is maybe carried out using hydrogen in the presence of a catalyst such as Raney nickel or palladium on carbon, in a reaction inert solvent such as methanol, ethanol or ethyl acetate, at an initial pressure of from about one to about four atmospheres and at a temperature of about 0° C. to about 60° C. Typically, the reaction Is conducted with methanol as the solvent and with about three atmospheres of hydrogen gas pressure at room temperature for about 0.5 to 1.0 hours.

The preparation of other compounds of the formula I not specifically described in the foregoing experimental section can be accomplished using combinations of the reactions described above that will be apparent to those skilled in the art.

In each of the reactions discussed or Illustrated in Schemes 1 and 2 above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The novel compounds of the formula I and the pharmaceutically acceptable salts thereof are useful as CRF at its receptor site in mammals, and therefore they are able to function as therapeutic agents in the treatment of the aforementioned disorders and diseases in an afflicted mammal.

The compounds of the formula I that are basic in nature are capable of forming a wide variety of different salts with various Inorganic and organic acids. Although such salts must be pharmaceutically acceptable for administration to animals, it is often desirable in practice reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. Stoichiometric quantities of reagents are preferably employed in order to ensure completeness of reaction and maximum yields of the desired final product.

The compounds of formula I and their pharmaceutically acceptable salts (the active compounds of this invention) may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formula I and their pharmaceutically acceptable carriers can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for compounds of the formula I and their pharmaceutically acceptable salts will depend on the intended route of administration and factors such as the age and weight of the patient, as generally known to a physician. The dosages will also depend on the particular Illness to be treated. For Instance, the daily dosage for stress-induced Illnesses, Inflammatory disorders, Alzheimer's disease, gastrointestinal diseases, anorexia nervosa, hemorrhagic stress and drug and alcohol withdrawal symptoms will generally range from about 0.1 to about 50 mg/kg body weight of the patient to be treated.

Methods that may be used to determine the CRF antagonist activity of the active compounds of this invention and their pharmaceutically acceptable salts are described in *Endocrinology*, 116, 1653–1659 (1985) and *Peptides*, 10, 179–188 (1985). The binding activities for compounds of formula I, II and III, expressed as $IC_{50}$ values, generally range from about 0.5 nanomolar to about 10 micromolar.

The present invention is Illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($^{13}$C NMR) were measured for solutions in deuterochloroform ($CDCl_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

The following abbreviations are used in the Examples: Ph=phenyl; iPr=isopropyl; HRMS=high resolution mass spectrum.

EXAMPLE 1

2',4',6'-Trimethyl-3-nitro-biphenyl-2-carboxylic acid methyl ester

Under a nitrogen atmosphere in 20 ml of anhydrous dimethoxyethane (DME) was combined 1.44 g (5.54 mmol) of methyl 2-bromo-5-nitrobenzoate 1.68 g (11.1 mmol) of cesium fluoride and 192 mg of tetrakis(triphenylphosphine) palladium(0). The reaction was stirred for 5 minutes, at which point 1.00 g (6.09) of mesitylboronic acid was added. The solution was heated to reflux for 20 hours, and was then cooled and fractionated on silica gel using 6:1 hexane: ethyl acetate (EtOAc) to afford, after concentration in vacuo and refractionation using toluene, 5.65 g (54%) of the title compound.

$^1$H NMR ($CDCl_3$) 1.93 (s-6H), 2.30 (s-3H), 3.57 (s-3H), 6.88 (s-2H), 7.47 (d-1H), 7.62 (dd-1H), 8.17 (d-1H).

EXAMPLE 2

2',4',6'-Trimethyl-3-nitro-biphenyl-2-carboxylic acid

Under a nitrogen atmosphere was combined 600 mg (2 mmol) of the title compound of Example 1 to 5 ml of THF, 3 ml of methanol and 5 ml of water. To this solution was added 320 mg (8 mmol) of sodium hydroxide and the resulting solution was heated to reflux for 96 hours. The reaction was cooled and concentrated in vacuo, diluted with water to a volume of 40 mls and extracted with ethyl acetate (1×25 ml). The acqeous layer was acidified to pH=1.5 with 6N hydrochloric acid (HCl) and the acqeous layer was extracted with ethyl acetate (2×25 ml). The organic extracts were washed with water (2×5 ml) and then with brine (1×5 ml), and then dried over magnesium sulfate, filtered and concentrated in vacuo to afford 526 mg (92%) of desired acid (the title compound).

$^1$H NMR ($CDCl_3$) 1.92 (s-6H), 2.31 (s-3H), 6.89 (s-2H), 7.47 (d-1H), 7.63 (dd-1H), 8.18 (d-1H).

EXAMPLE 3

(2',4',6'-Trimethyl-3-nitro-biphenyl-2-yl)-carbamic acid tert-butyl ester Under a nitrogen atmosphere In 20 ml of anhydrous benzene was combined 526 mg (1.85 mmol) of the title compound of Example 2 and 0.25 ml of triethylamine (TEA). To this suspension was added 398 µl (1.85 mmol) of diphenylphosphoryl azide, and the resulting solution was heated to reflux for 1 hour. The reaction mixture was cooled, 353 µl (3.70 mmol) of t-butanol was added, and the solution was heated to reflux for 16 hours. The crude reaction mixture was concentrated in vacuo and fractionated on silica gel using 5:1 hexane: EtOAc to afford, after concentration in vacuo, some pure product. Additional product was obtained in hexane triturations of product-containing fractions to afford 430 mg (65%) of the title compound.

$^1$H NMR ($CDCl_3$) 1.37 (s-9H), 1.93 (s-6H), 2.32 (s-3H), 6.08 (bs-1H), 6.96 (s-2H), 7.31 (m-2H), 7.89 (m-1H).

EXAMPLE 4

(3-Amino-2',4',6'-trimethyl-biphenyl-2-yl)-carbamic acid tert-butyl ester

To a methanol solution (35 ml) containing 430 mg (1.20 mmol) of the title compound of Example 3 was added 10% palladium on carbon (50 mg) and the solution was hydrogenated at 50 psi. After 30 minutes, the reaction was stopped and the resulting solution was filtered to remove the catalyst and concentrated in vacuo to afford 385 mg (98%) of the title compound as a white solid.

$^1$H NMR (CDCl$_3$) 1.38 (s-9H), 1.93 (s-6H), 2.31 (s-3H), 4.10 (bs-2H), 5.57 (bs-1H), 6.50 (d-1H), 6.77 (d-1H), 6.92 (s-2H), 7.10 (dd-1H).

EXAMPLE 5

[3-(1-Ethyl-propylamino)-2',4',6'-trimethyl-biphenyl-2-yl] carbamic acid tert-butyl ester Under a nitrogen atmosphere was combined 5 ml of acetic acid, 205 mg (0.62 mmol) of the title compound of Example 4 and 126 μl (1.25 mmol) of 3-pentanone, followed by 890 mg (6.29 mmol) of powdered sodium sulfate (Na$_2$SO$_4$). The solution was allowed to stir for 20 minutes, at which point 158 mg (0.75 mmol) of sodium triacetoxyborohydride (NaBH(OAc)$_3$) was added. The solution was allowed to stir for 45 minutes and was then quenched with aqueous bicarbonate (75 ml) and was extracted with ethyl acetate (2×30 ml). The organic extract was washed with water (1×25 ml) and then brine (1×25 ml), and then dried over Na$_2$SO$_4$, filtered and concentrated in vacuo to afford 232 mg of crude product, which was chromatographed on silica gel using 9:1 hexane:ethyl acetate to afford 186 mg (74.7%) of the title compound.

$^1$H NMR (CDCl$_3$) 0.98 (t-6H), 1.33 (s-9H), 1.57 (m-4H), 1.98 (s-6H), 2.32 (s-3H), 3.30 (m-1H), 4.18 (bs-1H), 5.30 (bs-1H), 6.39 (d-1H), 6.68 (d-1H), 6.92 (s-2H), 7.20 (dd-1H).

$^{13}$C NMR (CDCl$_3$) 10.13, 20.25, 21.05, 26.61, 28.03, 55,29, 80.03, 110.77, 117,19, 127.69, 128.11, 120.80, 135.79, 136.09, 136.57, 144.30, 153.60

EXAMPLE 6

N-3-(1-Ethyl-propyl)-2',4',6'-trimethyl-biphenyl-2,3-diamine

Under a nitrogen atmosphere was dissolved 124 mg (3 mmol) of the title compound of Example 5 in 1 ml of dichloromethane and the resulting solution was cooled to 0° C. Trifluoroacetic acid (10 mls) was added and the solution was allowed to warm to ambient temperature. After 1 hour, the reaction was concentrated in vacuo, the residue was dissolved in dichloromethane (40 mls) and the organic solution was washed with 1N sodium hydroxide (NaOH) (25 ml), dried over Na$_2$SO$_4$, filtered and concentrated in vacuo to afford 94.3 (100%) of crude title compound.

$^1$H NMR (CDCl$_3$) 0.93 (t-6H), 1.60 (m-4H), 1.98 (s-6H), 2.30 (s-3H), 3.08 (m-3H), 3.22 (m-1H), 6.39 (d-1H), 6.61 (d-1H), 6.82 (dd-1H), 6.95 (s-2H).

EXAMPLE 7

2-Ethyl-1-(1-ethyl-propyl)-4-(2,4,6-trimethyl-phenyl)-1H-benzimidazole

Under a nitrogen atmosphere was combined 47 mg (0.15 mmol) of the title compound of Example 6 in 2 ml of triethylorthopropionate. To this solution was added a drop of concentrated HCl. The solution was allowed to stir for 18 hours and was then concentrated in vacuo. Crude product was dissolved in 5 mls of EtOAc followed by 3 ml of ethyl ether (Et$_2$O) saturated with HCl. The solution was concentrated in vacuo and triturated with ether. The resulting solids were filtered and washed with ether to afford the title compound as its HCl salt.

$^1$H NMR (CDCl$_3$) 0.83 (t-6H), 1.33 (t-3H), 1.98 (s-6H), 2.00 (m-4H), 2.20 (m-2H), 2.32 (s-3H), 2.88 (q-2H), 4.08 (m-1H), 6.93 (m-3H), 7.18 (dd-1H), 7.42 (d-1H).

I claim:

1. A compound of the formula

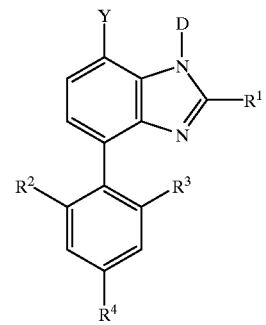

wherein D is hydrogen or ($_1$–C$_{10}$) straight or branched alkyl;

Y is hydrogen or methyl;

R$^1$ is hydrogen, halo, —S—(C$_1$–C$_6$)alkyl, or (C$_1$–C$_{10}$) straight or branched alkyl, wherein said alkyl may optionally be substituted with one or more substituents selected from chloro, fluoro, bromo, iodo, —S(C$_1$–C$_4$) alkyl, amino, —NH(C$_1$–C$_4$)alkyl and —N[(C$_1$–C$_4$) alkyl]$_2$;

R$^2$, R$^3$ and R$^4$ are selected, independently, from fluoro, chloro, (C$_1$–C$_6$)alkyl and (C$_1$–C$_6$)alkoxy; or two of R$^2$, R$^3$, and R$^4$ are hydrogen and the other is selected from hydroxy, iodo, bromo, formyl, cyano, nitro, trifluoromethyl, amino, (C$_1$–C$_6$)alkyl-O—(C$_1$–C$_6$) alkyl, —NHCH$_3$, —NH(CH$_3$)$_2$, —COCH, —COO (C$_1$–C$_4$)alkyl, —CO(C$_1$–C$_4$)alkyl, —SO$_2$—NH (C$_1$–C$_4$)alkyl, SO$_2$—N[(C$_1$–C$_4$)alkyl]$_2$, —SO$_2$NH$_2$, —NHSO$_2$—(C$_1$–C$_4$)alkyl, —S(C$_1$–C$_6$)alkyl and —SO$_2$—(C$_1$–C$_6$)alkyl, and wherein the (C$_1$–C$_4$) and (C$_1$–C$_6$)alkyl moieties in the foregoing R$^2$, R$^3$ and R$^4$ groups may optionally be substituted with one or two fluoro groups or with one substituent selected from hydroxy, amino, methylamino, dimethylamino and acetyl;

or a pharmaceutically acceptable salt of said compound.

2. A compound according to claim 1 wherein D is (C$_1$–C$_6$) straight or branched alkyl.

3. A compound according to claim 1 wherein Y is hydrogen.

4. A compound according to claim 1 wherein R$^2$, R$^3$ and R$^4$ are methyl, R$^1$ is methyl, ethyl or chloro and D is diethylmethyl.

5. A compound according to claim 1 wherein R$^1$ is methyl, ethyl or chloro.

6. A compound according to claim 1, wherein Y is hydrogen and R$^1$ is hydrogen, halo, —S—(C$_1$–C$_6$)alkyl or (C$_1$–C$_6$) straight or branched alkyl.

7. The compound of claim 1 wherein R$^2$, R$^3$ and R$^4$ are independently selected from fluoro, chloro, (C$_1$–C$_6$)alkyl and (C$_1$–C$_6$)alkoxy.

8. The compound of claim 7 wherein D is (C$_1$–C$_6$) straight or branched alkyl.

9. The compound of claim 7 wherein R$^1$ is methyl.

10. The compound of claim 7 wherein R$^1$ is ethyl.

11. The compound of claim 7 wherein R$^1$ is chloro.

12. The compound of claim 7 wherein Y is hydrogen and $R^1$ is hydrogen, halo, —S—$(C_1-C_6)$alkyl or $(C_1-C_6)$ straight or branched alkyl.

13. A compound of the formula

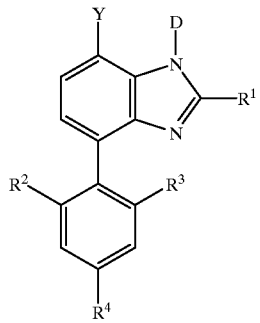

I wherein D is hydrogen or $(C_1-C_{10})$ straight or branched alkyl;

Y is hydrogen or methyl;

$R^1$ is hydrogen, halo, —S—$(C_1-C_6)$alkyl, or $(C_1-C_{10})$ straight or branched alkyl, wherein said alkyl may optionally be substituted with one or more substituents selected from chloro, fluoro, bromo, iodo, —S$(C_1-C_4)$alkyl, amino, —NH$(C_1-C_4)$alkyl and —N$[(C_1-C_4)$alkyl$]_2$;

$R^2$, $R^3$ and $R^4$ are selected, independently, from hydrogen, fluoro, chloro, $(C_1-C_6)$alkyl and $(C_1-C_6)$alkoxy and wherein the $(C_1-C_6)$alkyl moieties in the foregoing $R^2$, $R^3$ and $R^4$ groups may optionally be substituted with one or two fluoro groups or with one substituent selected from hydroxy, amino, methylamino, dimethylamino and acetyl; and wherein not more than one of said $R^2$, $R^3$ and $R^4$ is hydrogen, or a pharmaceutically acceptable salt of said compound.

* * * * *